United States Patent [19]

Seiler, Jr.

[11] Patent Number: 4,491,014

[45] Date of Patent: Jan. 1, 1985

[54] BOND TESTING APPARATUS

[75] Inventor: James F. N. Seiler, Jr., Frederick, Md.

[73] Assignee: The United States of America as represented by the Secretary of the Army, Washington, D.C.

[21] Appl. No.: 441,310

[22] Filed: Nov. 12, 1982

[51] Int. Cl.³ .................. G01N 19/04; G01N 3/10
[52] U.S. Cl. ................................. 73/150 A; 73/827
[58] Field of Search ............ 73/150 A, 827; 277/184; 180/127, 120, 122

[56] References Cited

U.S. PATENT DOCUMENTS

| | | | |
|---|---|---|---|
| 3,291,237 | 12/1966 | Hopkins et al. | 180/127 |
| 4,043,179 | 8/1977 | Ingle, Jr. | 73/37 |
| 4,077,489 | 3/1978 | Vaughen | 180/124 |
| 4,393,699 | 7/1983 | Seiler, Jr. | 73/827 |

FOREIGN PATENT DOCUMENTS 1455534 11/1976 United Kingdom ............ 73/150 A

Primary Examiner—Steven L. Stephan
Assistant Examiner—W. Morris Worth
Attorney, Agent, or Firm—John H. Raubitschek; Arthur I. Spechler; Werten F. W. Bellamy

[57] ABSTRACT

An apparatus for measuring the strength of a bond between a lamina and its substrate, or the like is shown and described. Air, or some other fluid under pressure, causes a gasket to protrude from a piston to seal the atmosphere from a chamber within the piston and the adjacent exposed lamina surface. The fluid also pressurizes this chamber to pull a loading fixture and a portion of the lamina attached thereto away from the substrate. The force required to pull the lamina from the substrate is equal to the strength of the bond.

5 Claims, 4 Drawing Figures

BOND TESTING APPARATUS

The invention described herein may be manufactured, used and licensed by or for the Government for governmental purposes without payment of any royalty thereon.

BACKGROUND OF THE INVENTION

1. Field of the Invention

This invention relates to testing apparatus and, more particularly, to apparatus for applying pneumatic pressure to a chamber within a piston to draw a loading fixture and attached lamina from a substrate to measure the bond strength, and the like.

2. Description of the Prior Art

There is a need for a simple, reliable and inexpensive device for measuring the strength of a bond, such as that which is formed between a lamina and its substrate. Illustratively, it is often important to measure the adherence to a surface of a layer of paint, varnish, adhesive, or the like, or even the adherence of a sheet to a cellular core (i.e. "honeycomb" construction). Field testing concrete through measuring the force required to draw concrete anchor from a recent pouring to determine the stability of the structure under examination also is quite important.

Through the years, a number of devices have been proposed to accomplish these purposes. Typically, these proposals suggest cumbersome apparatus that requires many specially manufactured parts. These devices are not only costly, but also are expensive and, nevertheless, quite frequently still fail to provide consistent data. As a general matter, these devices are not suited to field application because their bulk, weight, and lack of adaptability to irregular surfaces tend to prevent their use where there is the greatest need.

Clearly, a simple, inexpensive device to measure bond strengths on irregular surfaces with reproducible results is required.

SUMMARY OF INVENTION

These and other needs that have characterized the prior art are satisfied, to a great extent, through the practice of the invention. A typical embodiment of the invention has a generally cylindrical piston. One transverse surface of the piston has a centrally disposed chamber and a concentric annular recess that accommodates a longitudinally movable gasket. A loading fixture is mounted in the center of the chamber for attachment to the exposed lamina surface, concrete anchor or the like. Air, or another suitable fluid, is introduced under pressure into the annular recess to force the gasket to move in a longitudinal direction and press against the adjacent exposed lamina surface. The gasket forms a pneumatic seal that enables the pressure to increase within the chamber, effectively pressing the chamber away from the lamina while continuing to maintain an hermetic seal. Ultimately, the loading fixture tears the attached portion of the lamina from its substrate. Because the air pressure, transverse chamber area and loading fixture contact area are known, the bond strength, that is, the force required to separate the lamina from the substrate, or to extract the anchor from the concrete, can be determined with accuracy.

By reason of the inherent resiliency of the gasket, the apparatus characterizing the invention can adjust to pneumatically seal convex, concave, or other moderately irregular surfaces. Only the piston, the gasket and the loading fixture are required for the device that characterizes the invention, thereby reducing costs and increasing reliability. Test results obtained with this apparatus, moreover, show significantly greater consistency than that which has been demonstrated with other prior art devices.

Consequently, it is an object of the invention to provide an improved bond testing apparatus.

It is a further object of the invention to measure lamina bond integrity through the application of fluid under pressure.

It is still another object of the invention to provide a bond strength test apparatus that is adaptable to moderately curved surfaces.

DESCRIPTION OF THE PREFERRED EMBODIMENTS

Figure 1:
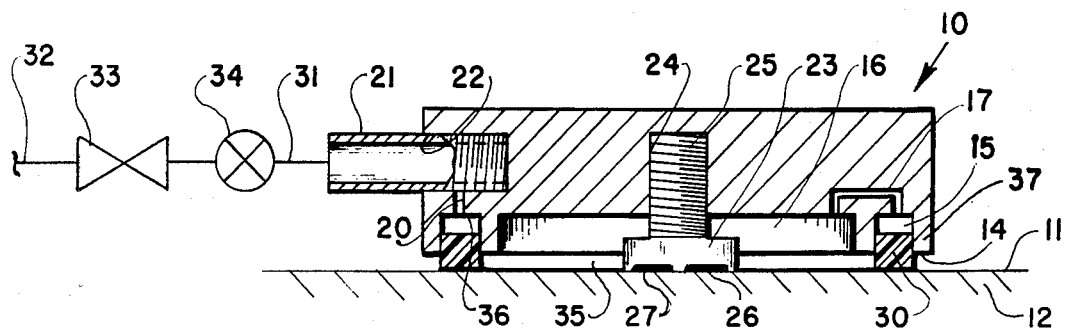
FIG. 1 is a front elevation in full section taken along the line 1—1 of FIG. 2 of a typical embodiment of the invention.

For a more complete appreciation of the invention, attention is invited to FIG. 1, which shows a piston 10 spaced immediately above a lamina 11, which lamina is bonded to a substrate 12. As illustrated, the piston 10 is generally cylindrical and has a longitudinal axis. A transverse end 14 of the piston 10 is spaced from the lamina 11 and has a peripherally disposed annular groove 15 which is concentric with the axis. A chamber 16 is formed in the transverse end 14 within the periphery of the groove 15. The chamber 16 is disk-shaped and also is concentric with the longitudinal axis.

A conduit 17 establishes fluid communication between the annular groove 15 and the chamber 16. An inlet conduit 20 provides fluid communication between the annular groove 15 and an inlet fitting 21 that is received in a tapped and threaded bore 22. In accordance with one aspect of the invention, the bore 22 penetrates the cylindrical surface of the piston 10 in a radial direction. Further in this respect, and also in accordance with a feature of the invention, it should be noted that the inlet conduit 20 (which communicates with the annular groove 15) and the conduit 17 (which establishes fluid communication between the groove and the chamber 16) are on diametrically opposite sides of the groove 15.

Actual operation of the piston 10 has produced satisfactory results with conduits 17,20 of 1/16 inch diameter. Preferably, the conduits 17,20 communicate with the annular groove 15 in which a radial width of ¼ inch and a longitudinal depth of ¼ inch have been found suitable for the purpose of the invention.

A loading fixture 23 is lodged in a threaded bore 24 that is formed in the piston 10 in alignment with the longitudinal axis. The bore 24 provides a means for attaching the loading fixture 23 to the piston 10. As illustrated, the loading fixture 23 protrudes through the chamber 16 and extends, in a longitudinal direction, slightly beyond the transverse end 14 in order to bear against the lamina 11. The loading fixture 23 has a threaded shank 25 that terminates in a larger diameter head 26. A transverse, flat surface 27 of the head 26 is fastened by means of a suitable adhesive to the lamina 11. In practice an epoxy glue known as "Scotchweld Structural Adhesive 1828" manufactured by 3M Company of Minnesota has been found quite satisfactory.

Typically, a glue, or adhesive, suitable for the invention must meet a few criteria. The bond between the flat surface 27 and the adjacent surface of the lamina 11 that the adhesive establishes must be stronger than the bond between the lamina 11 and the substrate 12. The bond that the adhesive forms, moreover, must be reasonably uniform in strength from sample-to-sample. Preferably, for consistent test results, the adhesive should be applied to the flat surface 27 and the adjacent portion of the lamina 11 in a layer of essentially constant thickness. This adhesive layer thickness also should be constant from sample-to-sample.

Figure 4:
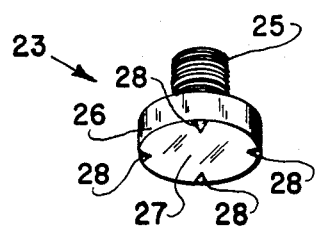
FIG. 4 is a perspective view of a loading fixture for use in connection with the embodiments of the invention shown in FIGS. 1 through 3.

Toward this end, attention is invited to FIG. 4 which shows the loading fixture 23 in a perspective view. Note that the flat surface 27 is provided with four protrusions 28 which are equidistantly spaced on the circumference of the head 26. The protrusions 28 all are of the same height above the flat surface 27 to enable the adhesive (not shown in FIG. 4) to fill the gap that the protrusions 28 form between the flat surface 27 and the adjacent portion of the lamina 11 (FIG. 1) in a uniformly thick layer. In this manner, a constant adhesive thickness is formed through the entire area that is defined by the flat surface 27 in a way, moreover, that is consistently reproducible.

Figure 2:
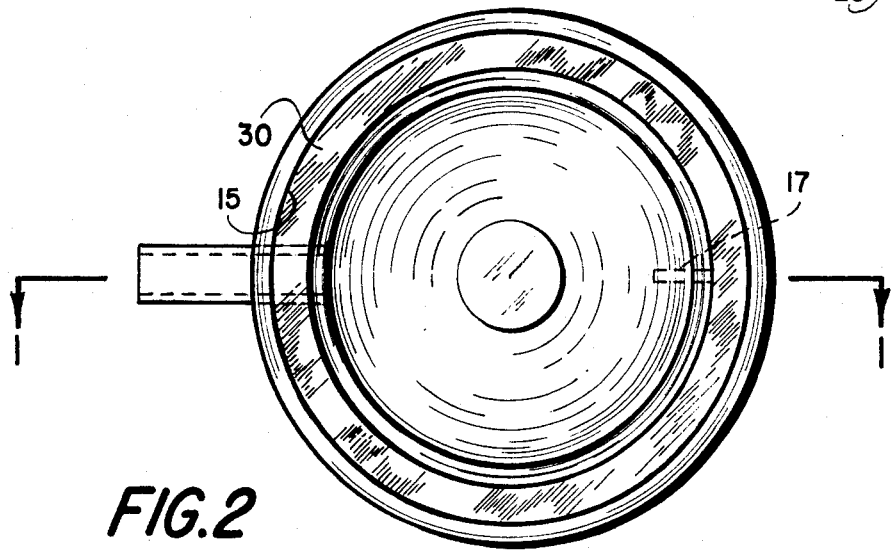
FIG. 2 is a bottom view of the device shown in FIG. 1.

In accordance with an important feature of the invention, attention is invited to FIG. 2. As shown in FIG. 2, an annular gasket 30 is seated in the groove 15. It has been found, for the purposes of the invention, that the gasket 30 is best formed by temporarily covering with tape or otherwise suitably blocking the apertures in the groove 15 that communicate with the conduits 17,20 (FIG. 1). The gasket 30 should be flexible, tight fitting within the groove 15, but also enjoy a low-friction contact with the longitudinal sides of the groove. It has been found, for example, that filling the groove 15 with "RTV 11 Silicone Rubber Compound", a product of the General Electric Company, and allowing this material to mold and set itself in place within the groove produces acceptable results.

Attention is once more invited to FIG. 1, which shows a flexible conduit 31 that establishes fluid communication between the inlet fitting 21 on the piston 10 and a suitably high pressure air supply 32 through a valve 33. A combination pressure gauge and recorder 34 also is coupled to the conduit to provide bond strength data as described subsequently in more complete detail.

In operation, the adhesive is applied to the lamina 11 and the loading fixture 23 is pressed into the fresh adhesive until the protrusions 28 (FIG. 4) bear perpendicularly against the adjacent surface of the lamina. Excess adhesive ordinarily would well up along the longitudinal surface of the head 26, and thereby introduce an uncontrollable effect that might influence test results. To prevent excess glue from adhering to the cylindrical surface of the head 26, a ring (not shown) of Teflon, or the like, is temporarily and snugly fitted to the cylindrical surface of the head. The outer surface of the ring is chamfered to produce a truncated conical profile. The apical portion of the ring is fitted on the head 26 in alignment with the tops of the protrusions 28.

Thus, as the loading fixture 23 and the temporarily associated ring are pressed against the lamina 11 (FIG. 1), the ring has the effect of shielding the cylindrical side of the head from excess adhesive 35. The excess adhesive 35 forms a moat that circumscribes the head 26. Because the adhesive will not bond with the Teflon ring, the ring is removed (after the adhesive has set) by manually withdrawing it from the head 26 in the direction of the longitudinal axis. In this way, the quantity, thickness and layer uniformity of the adhesive that joins the loading fixture 23 to the lamina 11 is carefully, albeit simply, controlled to provide a high degree of test sample consistency.

The threaded shank 25 of the loading fixture, after the glue has set and the Teflon ring has been removed, is screwed into the bore 24 in the piston 10 until the transverse end 14, or some portion of the transverse end, contacts the adjacent surface of the lamina. Contact between the transverse end 14, or a portion of that end, and the lamina 11 is not essential for the practice of the invention. Thus, a clearance of $\frac{1}{8}$ inch between the transverse end 14 and the lamina 11 has provided acceptable results with the gasket 30, and width and depth of the groove 15 described herein.

The valve 33 is opened to permit air to flow into the groove 15 by way of the inlet fitting 21 and the inlet conduit 20. Air, admitted to the groove 15 in the foregoing manner, presses the portion of the flexible gasket 30 that is next to the discharge from the inlet conduit 20 in a longitudinal direction to the adjacent surface of the lamina 11. This movement of the gasket 30 creates a small plenum 36 of high pressure air that progressively increases in volume as the gasket 30 is gradually, but very swiftly, pressed to protrude from the groove 15.

As previously noted, the conduit 17 that establishes fluid communication between the groove 15 and the chamber 16, is 180° away from the inlet conduit 20. In this way, it is believed, contact between the gasket 30 and the lamina 11 is essential complete before the gasket unblocks the inlet to the conduit 17 and permits air under pressure to flow through the conduit 17 in order to pressurize the chamber 16.

The resilient nature of the gasket 30 enables this gasket to adapt itself to irregular lamina surfaces and nevertheless form an hermetic seal with that surface. Thus, the apparatus that characterizes the invention can be used with consistently acceptable results on surfaces that depart from a plane. Illustratively, concave, convex and cylindrical surfaces, as well as the minor irregularities that are to be expected on any surface, are all suitable for bond testing with the apparatus described herein. Further in this respect, the pneumatic forces developed within the chamber 16 act upon the longitudinal surface of the gasket 30 in a radially outward direction. This force presses the outer longitudinal surface of the gasket 30 against an annular flange 37 that forms the outer wall of the groove 15 and the piston 10. Thus, the higher the air pressure within the chamber 16, the tighter the seal that is formed between the gasket 30, the flange 37 and the lamina 11.

The air pressure is increased, preferably at a constant rate, until a maximum pressure of about 100 pounds per square inch is generated within the chambers 15 and 16. The pneumatic pressure forces so generated are transferred to the interface between the lamina 11 and the substrate 12 by way of the bore 24 and the loading fixture 23 that is mounted in that bore. As a general matter, the strength of most lamina or bonds will be exceeded within this maximum. In this circumstance, the loading fixture 23 and the attached piston 10 will pull away from the lamina 11 and the substrate 12 in a direction that is perpendicular to the lamina surface in the direction of the longitudinal axis 13. In pulling away from the lamina 11, the head 26 will carry with it that portion of the lamina that is bonded to it by means of the adhesive.

Because the air pressure in the chamber 16 is known, the transverse area of the chamber is known and the contact area of the loading fixture 23 also is known, the force required to separate the lamina 11 from the substrate 12 directly under the head 26, and hence the strength of the lamina-substrate bond, can be calculated in the following manner:

$$F = P \times A$$

Where
F = force in pounds
P = air pressure in pounds per square inch
A = area of the piston in square inches

EXAMPLE $A_1$ = area of the loading fixture head (0.5 square inches)
$A_2$ = working area of the chamber 16 of the piston and the working area taken inside the annular groove 15 (7 square inches)
P = air pressure (100 pounds per square inch)
$A_2 - A_1$
7.0 − 0.5 = 6.5 square inches (effective area)
F = 100 pounds per square inch × 6.5 square inches
F = 650 pounds per square inch (bonding force)

Although the pressure gauge and recorder 34 shown in FIG. 1 provide a record of the air pressure in the chamber 16 at the time the lamina separates from the substrate 12 from which bond strength can be calculated in the manner indicated above, the recorder 34 also can be calibrated to provide a direct readout in pounds (or other measure) of bonding force.

To restore the apparatus to a reusable condition, the loading fixture 23 is removed from the piston. The lamina adhering to the flat surface 27 is broken up and the entire fixture is boiled in distilled water to soften the adhesive to a degree to which it can be scraped from the head 26. A disposable loading fixture that is discarded after only one use also is suitable for application to the invention.

The gasket 30, moreover, can be manually pressed back into the groove 15 after the air supply 32 is uncoupled from the inlet fitting 21 by closing the valve 33.

Figure 3:
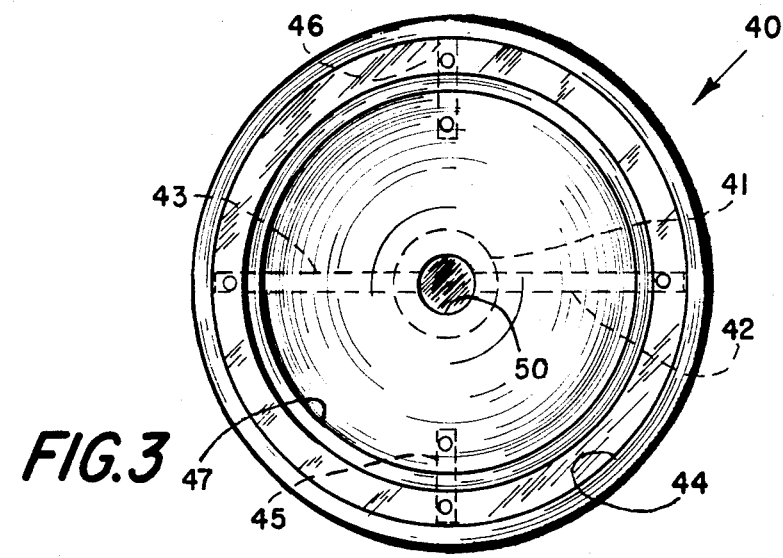
FIG. 3 is a bottom view of another embodiment of the invention.

An alternate embodiment of the invention is shown in FIG. 3. Illustratively, a piston 40 has a generally cylindrical shape. An inlet fitting 41 is centrally disposed on the top of the piston 40 in alignment with the piston's longitudinal axis. The inlet fitting establishes fluid communication with a pair of radial bores 42,43 that are oriented in diametrically opposite directions. Fluid communication is provided through the bores 42,43 to an annular groove 44 in which the flexible gasket (not shown in FIG. 3) is seated.

A pair of smaller bores 45,46, oriented perpendicular to the bores 42,43, provide fluid communication from the annular groove 44 to a concentric, inwardly disposed chamber 47. As shown in the drawing, a loading fixture bore 50 is formed in the center of the piston 40, concentric with the chamber 47 and the annular groove 44. A suitable loading fixture (not shown in the drawing) is threaded into the bore 50 after being bonded to the lamina (also not shown in the drawing), or other surface that is to be tested.

The apparent advantage of the embodiment of the invention shown in FIG. 3 is the more uniformly distributed air pressure that the central air inlet fitting 41 applies to the test apparatus. The eccentrically mounted side inlet fitting 21 (FIG. 1) may impose eccentric loads on the piston 10 that introduce inaccuracies.

To improve the portability of the pistons 10,40 (FIGS. 1 and 3) the bores 17,20 and 42,43,45,46 can be angularly oriented relative to transverse ends of the respective piston that are to be spaced from laminae. This will enable excess metal to be machined, or otherwise removed, from the opposite transverse ends of the individual pistons, thereby producing a significant weight saving.

I claim:

1. A system for measuring the bond strength of material adhered to a substrate comprising:
   a supply of fluid under pressure, a pressure responsive device in fluid communication with said supply for producing an indication of the bond strength of the material with respect to the substrate,
   a piston in fluid communication with said supply and said pressure responsive device, said piston having a surface with a peripheral groove formed therein, a conduit establishing fluid communication with said supply and said pressure responsive device, said piston having a chamber formed in said surface, said chamber being formed inwardly of said peripheral groove and in fluid communication therewith,
   a resilient gasket filling said peripheral groove for forming a fluid tight seal between said piston and the material to be measured, and
   means attached to said piston for transferring fluid pressure forces to the material.

2. A system of the type described in claim 1, wherein said means comprises:
   a loading fixture selectively connected to said piston, and
   a head formed on said loading fixture, said head having a flat surface for being joined to the material, the bond strength of which is to be measured.

3. A piston for measuring the bond strength of material adhered to a substrate through fluid pressure comprising:
   a surface on the piston transverse to the longitudinal axis of the piston, said surface having a peripheral groove formed therein to form a fluid pressure seal, said surface also having a chamber formed therein inward of said peripheral groove, said chamber and said groove being in fluid communication in order to apply the fluid pressure to the material,
   an inlet fitting penetrating said piston to establish fluid communication with said peripheral groove,
   a resilient gasket filling said peripheral groove for forming a fluid tight seal between said piston and the material that is to be measured, and
   means attached to said piston for transferring the fluid pressure forces within the piston to the material.

4. A piston according to claim 3 wherein said inlet fitting is centrally disposed on said piston with respect to said peripheral groove and said chamber.

5. A piston according to claim 3 wherein said inlet fitting is eccentrically disposed on said piston with respect to said groove and said chamber.

* * * * *